(12) United States Patent
Manri et al.

(10) Patent No.: US 11,427,850 B2
(45) Date of Patent: Aug. 30, 2022

(54) MICROORGANISM TEST (71) Applicant: HITACHI, LTD., Tokyo (JP)

(72) Inventors: Chihiro Manri, Tokyo (JP); Hideyuki Noda, Tokyo (JP); Naoko Senda, Tokyo (JP)

(73) Assignee: HITACHI, LTD., Tokyo (JP)

( * ) Notice: Subject to any disclaimer, the term of this patent is extended or adjusted under 35 U.S.C. 154(b) by 91 days.

(21) Appl. No.: 16/298,789

(22) Filed: Mar. 11, 2019

(65) Prior Publication Data
US 2020/0040374 A1 Feb. 6, 2020

(30) Foreign Application Priority Data
Aug. 6, 2018 (JP) .............. JP2018-147846

(51) Int. Cl.
C12Q 1/06 (2006.01)
C12Q 1/66 (2006.01)

(52) U.S. Cl.
CPC .................. *C12Q 1/06* (2013.01); *C12Q 1/66* (2013.01)

(58) Field of Classification Search
CPC ....................................................... C12Q 1/06
See application file for complete search history.

(56) References Cited

U.S. PATENT DOCUMENTS 5,891,702 A    4/1999   Sakakibara et al.

FOREIGN PATENT DOCUMENTS

| CN | 101639479 A | * | 2/2010 | ........... G01N 33/569 |
|---|---|---|---|---|
| EP | 1134291 A1 | * | 9/2001 | ............... C12Q 1/66 |
| JP | H09182600 A | | 7/1997 | |
| JP | 2000157295 A | | 6/2000 | |
| WO | 2000/071675 A1 | | 11/2000 | |
| WO | 2006/044895 A1 | | 4/2006 | |
| WO | WO-2006044895 | * | 4/2006 | ............... C12Q 1/04 |
| WO | 2011/070507 A1 | | 6/2011 | |

OTHER PUBLICATIONS

Search Report for related European Patent Application No. 19161445.2, dated Sep. 9, 2019; 6 pages.
Office Action dated Sep. 7, 2021 in counterpart JP Patent Application No. 2018-147846, 4 pages.
Office Action dated Jan. 18, 2022 in counterpart JP Patent Application No. 2018-147846, 8 pages.
P-03-103, "Ensuring Microbial Safety of Regenerative Medicine: Development of a Rapid Sterility Test Method", The 17th Congress of the Japanese Society for Regenerative Medicine, Programme and Abstracts, Poster 42, Mar. 23, 2018.

* cited by examiner

*Primary Examiner* — Robert J Yamasaki
(74) *Attorney, Agent, or Firm* — Procopio, Cory, Hargreaves & Savitch LLP (57) ABSTRACT Provided is a method for detecting a microorganism in a test sample containing cells, including a step of adding the sample to a microorganism culture medium, a step of culturing the microorganism culture medium containing the sample, a step of sampling a part of the culture medium at a predetermined time, a step of acquiring the ATP level of the sampled culture medium, and a step of detecting the microorganism in the sample based on the change of the ATP level over time.

5 Claims, 6 Drawing Sheets

MICROORGANISM TEST

RELATED APPLICATION

This application claims the benefit of priority to Japanese Patent Application number 2018-147846, filed Aug. 6, 2018, hereby incorporated by reference in its entirety.

TECHNICAL FIELD

The present disclosure relates to a method and a kit for detecting a microorganism contained in a biological sample containing cells using ATP bioluminescence method.

BACKGROUND ART

The sterility tests listed in the Pharmacopoeia are mainly based on culturing methods, and there are cases when it takes 14 days or longer to obtain results, thus, a rapid sterility test has been required. For example, there are cases where preparations requiring rapid administration to patients such as regenerative medical products and blood preparations and preparations having short usage periods have been used in circumstances in which there is no verification of sterility at the time. Further, biopharmaceuticals (antibody drugs, nucleic acid drugs and the like) produced using a cell (including animal, plant, and insect) culture involve the risk of microorganism contamination during the production process, thus, achieving microorganism monitoring during the process may be useful for saving time and loss, and accordingly, rapid sterility tests have been required.

There is a method which uses an ATP bioluminescence method as one of the rapid sterility tests. This method uses the ATP (adenosine triphosphate) possessed by an organism within the cells, and luciferase or luciferin which are chemiluminescent and produce light, in order to measure the luminescence produced by the reaction of the ATP in cells with luciferase and luciferin, and calculate the presence and number of organisms based on the amount of luminescence. The ATP bioluminescence method is an enzymatic reaction, and thus, is excellent in sensitivity and rapidity, but in the cases of cell preparations such as the above mentioned regenerative medical products, blood preparations, and cell culture monitoring, cells are present in the test samples, thus, the ATP derived from the cells becomes background noise, and accordingly, it is difficult to detect the microorganism-derived ATP.

As a technique for detecting microorganism-derived ATP in the presence of cells, there is, for example, a method which uses a surfactant (WO 00/071675 A, and WO 2011/070507 A). In detail, Tween 80, Triton X-100, sodium dodecyl sulfate (SDS) and the like are added to and treated with the test sample, and the cells are selectively destroyed to detect the ATP derived from the microorganism.

Further, as another technique, there is a filter method (WO 2006/044895 A). In detail, by filtering a sample with a filter having a pore size of $\phi 4$ to 10 µm, the cells are trapped by a filter, and the bacteria in the filtrate is recovered. Then, the bacteria are detected based on the ATP derived from bacteria.

SUMMARY OF INVENTION

When examining a microorganism in a test sample containing cells, the ATP derived from cells becomes background noise, thus, the detection of the microorganism-derived ATP is difficult. In WO 00/071675 A and WO 2011/070507 A, a surfactant is used to selectively destroy cells, but there is the possibility of actually destroying the microorganism simultaneously. In the filter method shown in WO 2006/044895 A, cells of a size less than $\phi 4$ µm are also actually present, thus, it is difficult to completely separate the cells and the bacteria.

Further, the microorganism to be detected is a microorganism present in an extremely small amount in the test sample, but the ATP contained in one microorganism is a low level of approximately 1 amol.

Furthermore, a negative determination showing that the microorganism is not present in the test sample has not been established by the current technology.

As stated above, it is an object of the present disclosure to provide a method and means which uses an ATP bioluminescence method to detect the ATP derived from a microorganism in a test sample in which cells are present, and detect a microorganism in the test sample. Further, it is the object to provide a method and means which makes a negative determination when there are no microorganisms present in the test sample.

The present inventors have focused on the fact that when a test sample containing cells is not contaminated with a microorganism, the cells in the sample die after a certain period of time by culturing the sample in a microorganism culture medium, and the ATP level in the culture solution decreases, whereas when the sample is contaminated with the organism, the microorganism proliferates in the sample after a certain period of time and the ATP level in the culture solution increases. Thus, they found that the microorganism in a sample containing cells could be detected by obtaining the change of the ATP level over time in the culture solution. Therefore, in order to solve the aforementioned problems, the ATP level in a culture solution is measured after a sample containing cells is cultured in a microorganism culture medium according to the present disclosure.

In one embodiment, the present disclosure provides a method for detecting a microorganism in a test sample containing cells, including:

a step of adding the sample to a microorganism culture medium;

a step of culturing the microorganism culture medium containing the sample;

a step of sampling a part of the culture medium at a predetermined time;

a step of acquiring the ATP level of the sampled culture medium; and a step of detecting the microorganism in the sample based on the change of the ATP level over time.

Further, in a separate embodiment, the present disclosure provides a method for detecting a microorganism in a test sample containing cells, including:

a step of adding the sample to a microorganism culture medium;

a step of culturing the microorganism culture medium containing the sample;

a step of acquiring the ATP level of the entire amount of the culture medium after culturing; and a step of determining the presence or absence of the microorganism in the sample based on the ATP level.

Furthermore, in a separate embodiment, the present disclosure provides a kit for detecting a microorganism in a test sample containing cells, including a microorganism culture medium and an ATP detection reagent.

According to the present disclosure, the ATP level derived from a microorganism can be acquired and the microorganism in a test sample can be detected even if cells are present in the test sample. Further, when the microorganism is not present in the test sample, the test sample can be determined to be negative for the microorganism. Sterility tests which use the method and the kit of the present disclosure can contribute to rapidly confirming and maintaining the sterility of cell preparations which require rapid administration to patients such as regenerative medical products and blood preparations. Therefore, the present disclosure is useful in fields such as pharmaceutical manufacturing and regenerative medicine.

DETAILED DESCRIPTION

The present disclosure relates to a method and a kit for detecting a microorganism in a test sample containing cells. The test sample containing the cells is cultured in a microorganism culture medium, and the change of the ATP level over time is acquired. Due to the microorganism culture medium, the cells die when being cultured, and the ATP level derived from the cells decreases. When no microorganism is included in the test sample, the change of ATP over time tends to become a declining or a constant value, thus, it can be determined that the likelihood of being negative for the microorganism is high. When a microorganism is included in the test sample, the change of ATP over time tends to increase, thus, it can be determined that the test sample is positive for the microorganism. With respect to the sample in which the likelihood of being negative is high, a negative determination becomes possible by acquiring the ATP level of the entire sample at the end of culturing. The ATP level derived from the microorganism can be acquired by this configuration even if cells are present in the test sample. This is specifically described below.

In one embodiment, the present disclosure provides a method for detecting a microorganism in a test sample containing cells, including:

a step of adding the sample to a microorganism culture medium;

a step of culturing the microorganism culture medium containing the sample;

a step of sampling a part of the culture medium at a predetermined time;

a step of acquiring the ATP level of the sampled culture medium; and a step of detecting the microorganism in the sample based on the change of the ATP level over time.

As used herein, the "microorganism" which is a target for detection refers to at least one type of various types of microorganisms including bacteria, actinomycetes, fungi and the like. However, viruses are not included in the microorganism. Specifically, the microorganisms are the microorganisms listed in the pharmacopoeia as targets for detection by sterility tests, and the microorganisms such as pathogenic bacteria and pathogenic fungi which are targets for examination in examination rooms in hospitals, etc. For example, the microorganism may include bacteria and fungi such as *Propionibacterium* (as a specific example, *Proprionobacter acnes*), *Staphylococcus* (as specific examples, *Staphylococcus aureus* and *Staphylococcus epidermidis*), *Micrococcus, Streptococcus* (as a specific example, *Streptococcus pyogenes*, and *Streptococcus pneumoniae*), *Enterococcus* (as specific examples, *Enterococcus faecium* and *Enterococcus faecalis*), *Neisseria* (as specific examples, *Neisseria gonorrhoeae* and *Neisseria meningitidis*), *Moraxella, Escherichia* (as a specific example, *Escherichia coli*), *Shigella* (as specific example, *Shigella dysenteriae*, and *Shigella flexneri*), *Salmonella* (as specific examples, *Salmonella enterica* Typhi, *Salmonella enterica* subsp. *Paratyphi A*, and *Salmonella enteritidis*), *Citrobacter, Klebsiella* (as a specific example, *Klebsiella pneumoniae*), *Enterobacter, Serratia* (as a specific example, *Serratia marcescens*), *Proteus, Providencia, Morganella, Yersinia* (as a specific example, *Yersinia pestis*), *Vibrio* (as specific examples, *Vibrio cholerae, Vibrio parahaemolyticus, Vibrio vulnificus*, and *Vibrio mimicas*), *Aeromonas, Pseudomonas* (as a specific example, *Pseudomonas aeruginosa*), *Acinetobacter* (as a specific example, *Acinetobacter baumannii*), *Alcaligenes, Agrobacterium, Flavobacterium, Haemophilus* (as a specific example, *Haemophilus influenzae*), *Pasteurella, Francisella, Bordetella* (as a specific example, *Bordetella pertussis*), *Eikenella, Brucella, Streptobacillus, Actinobacillus, Legionella* (as a specific example, *Legionella pneumophila*), *Bacillus* (as specific examples, *Bacillus subtilis, Bacillus anthracis*, and *Bacillus cereus*), *Corynebacterium* (as a specific example, *Corynebacterium diphtherias*), *Lactobacillus, Listeria, Erysipelothrix, Nocardia, Actinomyces, Clostridium* (as specific examples, *Clostridium perfringens* and *Clostridium sporogenes*), *Bacteroides* (as a specific example, *Bacteroides fragilis*), *Fusobacterium, Mycobacterium* (as a specific example, *Mycobacterium tuberculosis*), *Campylobacter, Helicobacter* (as a specific example, *Helicobacter pylori*), *Spirillum, Treponema, Borrelia, Leptospira, Mycoplasma* (as a specific example, *Mycoplasma pneumonia*), *Aspergillus* (as specific examples, *Aspergillus niger* and *Aspergillus brasiliensis*), yeast (as a specific example, *Candida albicans*), but other microorganisms can also be the target for detection.

The test sample is not specifically limited as long as it is a sample containing cells. As used herein, "cells" do not include microorganisms which are the target for detection. Specifically, the test sample may include a biological sample derived from an organism, a sample which is suspected of being contaminated with a microorganism, and a sample which should be determined to be negative for the presence of a microorganism. For example, the test sample may be various samples such as blood, urine, bone marrow fluid, semen, milk, amniotic fluid, tears, biopsy tissue, cell culture solution, and cell culture supernatant. Further, the origin of the test sample is not specifically limited, the test sample may be derived from any species. For example, the test sample may be a sample derived from at least one organism of various species such as animals, plants, and insects. When the test sample is a liquid sample, it may be used as is, or can be diluted with a solvent or concentrated. When the test sample is a solid sample, it may be suspended in a solvent, homogenized with a grinder and the like, or a supernatant obtained by stirring the solid sample with a solvent may be used.

The term "detection" means determining whether or not a microorganism is present in the test sample containing the cells, measuring the microorganism in the test sample quantitatively or semi-quantitatively, and/or determining that the microorganism is not present in the test sample (microorganism negativity). The concentration of the microorganism which is likely to be contained in the test sample is not specifically limited.

In the present method, the test sample containing cells is added to a microorganism culture medium. The microorganism culture medium is a culture medium in which the microorganism to be detected can grow, but the cells contained in the test sample cannot grow. This kind of microorganism culture medium is well-known in the art, and is not specifically limited as long as it is a microorganism culture medium which has been used in existing sterility tests. For example, it may be a microorganism culture medium prescribed in the pharmacopoeia, specifically, Soybean-Casein Digest (SCD) culture medium, Sabouraud-Dextrose liquid culture medium, Fluid Thioglycollate culture medium, Lactose broth and the like can be used. The microorganism culture medium can be appropriately selected by a person skilled in the art in accordance with the type of cells contained in the test sample, and the type and the assumed amount of the microorganism which is likely to be present. It may be desirable that the amount of the test sample to be added to the microorganism culture medium is also appropriately adjusted in accordance with the type of cells which can be included, the type and the assumed amount of the microorganism which is likely to be present, the microorganism culture medium to be used, the culture time and the like.

Then, the microorganism culture medium (culture solution) to which the test sample is added is cultured. The culturing can be performed under the conditions (temperature, time, aerobic or anaerobic, stationary or shaking) which are conventionally used in the art. Specific culturing conditions may be different in accordance with the type of a target microorganism, the test sample or the type of cells, and the type of microorganism culture medium to be used and the like, and can be appropriately set by a person skilled in the art. The culture time may be specifically 1 to 48 hours, preferably 1 to 30 hours, and more preferably 1 to 24 hours. The culture time may vary depending on the amount and the type of microorganism to be detected, the type of cells contained in the test sample, the microorganism culture medium to be used, the culture temperature, the purpose of the detection (whether or not there is a determination of negativity) and the like. As a control (standard culture), a culture medium (culture solution) to which the test sample is not added, a culture medium (culture solution) to which a sample containing a known microorganism at a known concentration or the like may preferably be cultured.

After the start of culturing, a part of the culture medium (culture solution) may be sampled at a predetermined time. In the same manner as the culture time, the time for sampling may also be dependent upon the amount and the type of microorganism to be detected, the type of cells contained in the test sample, the microorganism culture medium to be used, the culture temperature, the purpose of the detection and the like, and sampling may be performed at least once, for example 1 to 10 times at an interval of 10 minutes to 20 hours, preferably at an interval of 30 minutes to 15 hours. The time intervals of the samplings may or may not be equally spaced.

The ATP level may be acquired for the sampled culture medium (culture solution). The acquisition of the ATP level can be performed by a well-known ATP luminescence measurement method. Specifically, luciferase and luciferin which chemically react with ATP to produce light are used, the luminescence produced by the reaction of the ATP in the cells with luciferase and luciferin is measured, and the ATP level, and furthermore, the number of cells is determined based on the amount of luminescence. This kind of measurement of the ATP level can be readily performed by a person skilled in the art using a commercially available ATP detection reagent or kit and the like. As a pretreatment, ATP other than the ATP derived from the living microorganism may preferably be removed, for example, by adding ATPase to the sampled culture solution, and optionally adding methanol at the same time in order to increase the ATP in the living cells (described in detail in WO 2013/084772 A). Next, a well-known ATP extraction solution (for example, trichloroacetic acid, a surfactant, a lysozyme and the like) may be used to extract the ATP in the cells. Then, the extracted ATP may be made to emit light using the luciferin-luciferase luminescence reaction. Specifically, a luminescent reagent containing luciferin and luciferase may be added to the sample. Luminescence may be produced by reacting the luminescent reagent with the extracted ATP, thus, the amount of luminescence may be measured. The luminescent reagent is also known in the art, and is not specifically limited. The measurement of the luminescence can be performed by a luminescence measurement method known in the art, for example, using a luminometer or a luminescence plate reader, or by photon counting which uses a photomultiplier tube. The ATP level in the culture solution may be acquired based on the measurement value of the amount of luminescence.

Figure 3:
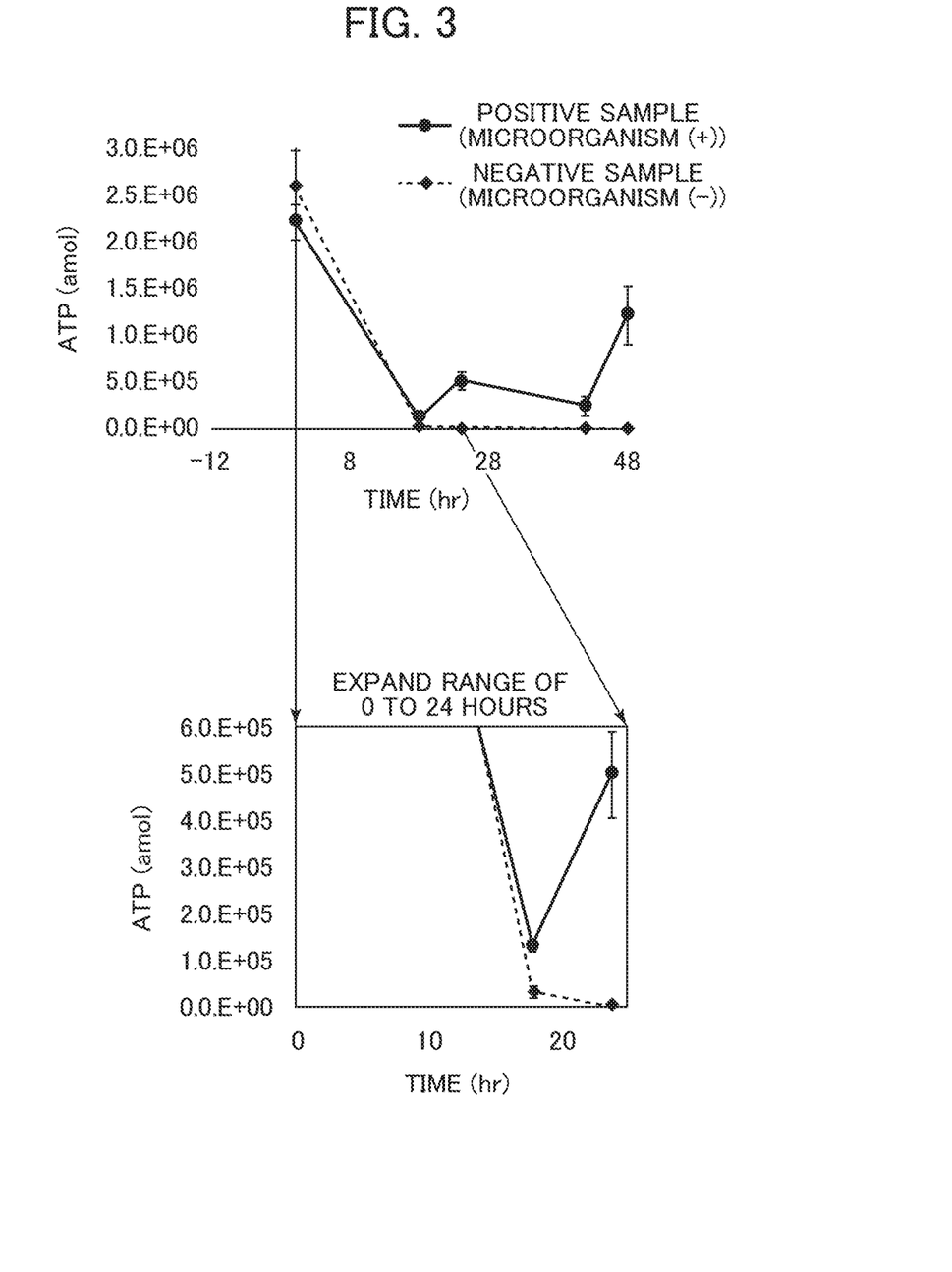
FIG. 3 is graph showing an example of the ATP change over time.

Then, the change of the ATP level over time of the sampled culture medium may be obtained. The culture medium to be used is the microorganism culture medium, thus, the cells contained in the test sample die when culturing, and the ATP level derived from cells decreases. When there is no microorganism contained in the test sample, the change of the ATP over time tends to become a declining or a constant value, thus, it can be determined that the likelihood of being negative for the microorganism negative is high. When a microorganism is contained in the test sample, the change of the ATP over time tends to increase following the proliferation of the microorganism, thus, it can be determined to be positive for the microorganism. FIG. 3 shows a specific example of the change of the ATP level over time.

Therefore, it is determined whether the change of the ATP level over time after the time when it becomes possible to determine the presence or absence of the microorganism tends to be a declining or a constant value, or tends to increase. For example, the slope can be obtained between two different points of the sampling. Therefore, it becomes possible to detect the microorganism in a sample from the change of the ATP level over time.

Further, in a separate embodiment, the present disclosure provides a method for detecting a microorganism in a test sample containing cells, including:

a step of adding the sample to a microorganism culture medium;

a step of culturing the microorganism culture medium containing the sample;

a step of acquiring the ATP level of the entire amount of the culture medium after culturing; and a step of determining the presence or absence of the microorganism in the sample based on the ATP level.

The step until the steps of adding to the microorganism culture medium and culturing can be performed in the same manner as the aforementioned method. After culturing, the ATP level of the entire amount of the culture medium (culture solution) is acquired. The acquisition of the ATP level of the entire amount of the culture solution can be performed by a conventional method such as performing the ATP luminescence measurement method after using, for example, a membrane filter to concentrate the culture solution. The presence or absence of the microorganism in the test sample may be determined based on the obtained ATP level. Specifically, when the obtained ATP level is low (for example, at the threshold or less), it means that the microorganism is not present, and determines that the test sample is negative for the microorganism. When the obtained ATP level is high (for example, above the threshold), it means that the microorganism is present in the test sample, and determines that the test sample is positive for the microorganism. This threshold may be different depending on the type and concentration of the cells contained in the test sample, the type and the amount of the test sample, culture time (culture end time) and the like, but it is possible to set in advance by a preliminary examination by a person skilled in the art.

As described above, the method according to the present disclosure can acquire the ATP level derived from the microorganism even if cells are present in the test sample, and can detect the microorganism in the sample. It is possible to detect a microorganism in the test sample containing cells rapidly and easily compared to conventional sterility tests (culture method) and rapid sterility tests. Furthermore, it can be determined that a test sample containing cells is negative for the microorganism.

The aforementioned method can be carried out easily and rapidly using the kit of the present disclosure. The kit of the present disclosure, i.e., the kit for detecting a microorganism in a test sample containing cells is characterized in containing a microorganism culture medium and an ATP detection reagent. The microorganism culture medium may be, as described above, a microorganism culture medium specified in, for example the pharmacopoeia, and specifically, is appropriately selected in accordance with the type of cells contained in the test sample, and the type and the assumed amount of the microorganism likely to be present. The ATP detection reagent may preferably include an ATP extraction solution and an ATP luminescent reagent. Further, the ATP detection reagent may be comprised of methanol, sugar (for example, at least one selected from the group consisting of glucose, fructose and sucrose), and alanine, or ATPase. ATP detection reagents may preferably be packaged together. The form of each component contained in the kit may be any form such as a solution, a powder, or a granule. Preferably, the respective components may be contained in the forms and concentrations suitable for carrying out the method of the present disclosure. The kit of the present disclosure may also further include instructions for carrying out the method for detecting a microorganism in a test sample containing cells.

Furthermore, the present disclosure provides a system for carrying out the above described method. Specifically, this kind of system is provided with:

a culture unit containing a culture container for culturing a microorganism culture medium to which a test sample containing cells is added;

an ATP detection device for acquiring the ATP level of the culture medium;

an analysis unit which is configured to determine the microorganism in the test sample containing the cells based on the ATP level in the culture medium acquired by the ATP detection device; and a means for sampling the culture medium from the culture container.

The culture unit contains one or a plurality of culture containers for culturing the microorganism culture medium. The microorganism culture medium to which the test sample containing the cells is added may be introduced to the respective culture containers. As a control (standard culture), the culture unit may be provided with a culture container containing the microorganism culture medium to which the test sample containing cells is not added.

The ATP detection device used in the system according to the present disclosure is not specifically limited as long as it is a device used in an ATP luminescence measurement method. Generally, a luminometer, a luminescence plate reader, or a photomultiplier tube may be used. Further, if a plurality of culture containers are prepared in the culture unit, the ATP detection device acquires the ATP levels for each of the plurality of culture containers.

The system according to the present disclosure may contain a means for sampling the microorganism culture medium (a part or the entirety) from each culture container of the culture unit. Further, the system according to the present disclosure may contain an ATP luminescence reaction unit for performing the ATP luminescence measurement method. For example, the ATP luminescence reaction unit may include a means for introducing the ATP detection reagent (ATPase, ATP extraction solution, ATP luminescent reagent and the like).

The analysis unit may be configured to analyze the ATP level obtained by the ATP detection device, and to determine the presence or absence of the microorganism in the test sample, or verify that the test sample is negative for the microorganism. The analysis unit may be configured to obtain the change of the ATP level over time, when analyzing the ATP level. If a plurality of culture containers are prepared in the culture unit, the analysis unit may be configured to analyze the analysis results of the respective culture containers obtained from the ATP detection device. Alternatively, the analysis unit may be configured to compare the ATP level obtained by the ATP detection device with a database, and detect the microorganism in the test sample based on the result thereof.

The system according to the present disclosure may be provided with a mechanism for transporting the microorganism culture medium between the culture unit, the ATP luminescence reaction unit and the ATP detection device.

Furthermore, the system according to the present disclosure may be provided with a control unit which is configured to control and operate the entire system. Further, the system may be provided with a means for displaying, outputting or storing the results obtained in the analysis unit, for example, one or more selected from the group consisting of an input unit, a display unit, an output unit, and a storage unit may be attached to the control unit.

Specific embodiments of the method used in the present disclosure are described below.

[First Embodiment] Method for Acquiring the Microorganism-Derived ATP Level

Figure 1:
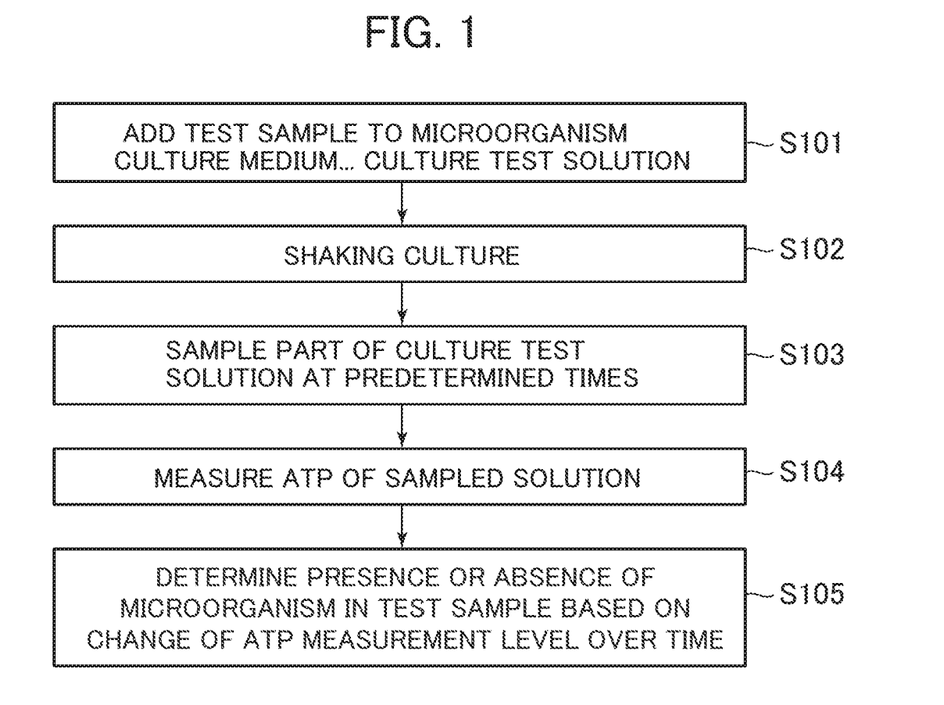
FIG. 1 illustrates a flowchart of a method according to a first embodiment.

FIG. 1 is a drawing describing a method for acquiring microorganism-derived ATP level according to the present disclosure.

In Step S101, a test sample is added to a microorganism culture medium. The microorganism culture medium may use, for example, the Soybean-Casein Digest (SCD) culture medium, the Sabouraud-Dextrose liquid culture medium and the like which have been used in existing sterility tests.

In Step S102, the culture test solution of Step S101 is set in a thermostatic chamber and cultured. Depending on the species of the microorganism to be detected, a shaking culture may be preferred.

In Step S103, a part of the culture test solution is sampled at predetermined times.

In Step S104, the ATP in the sampled solution is measured. The ATP measurement may be conducted by using a known technology or system, for example, a Rapid Microbial Testing System "Lumione BL-1000".

In Step S105, the presence or absence of the microorganism in each test sample is determined based on the change of the ATP level over time of each culture test solution acquired in Step S104.

Figure 2:
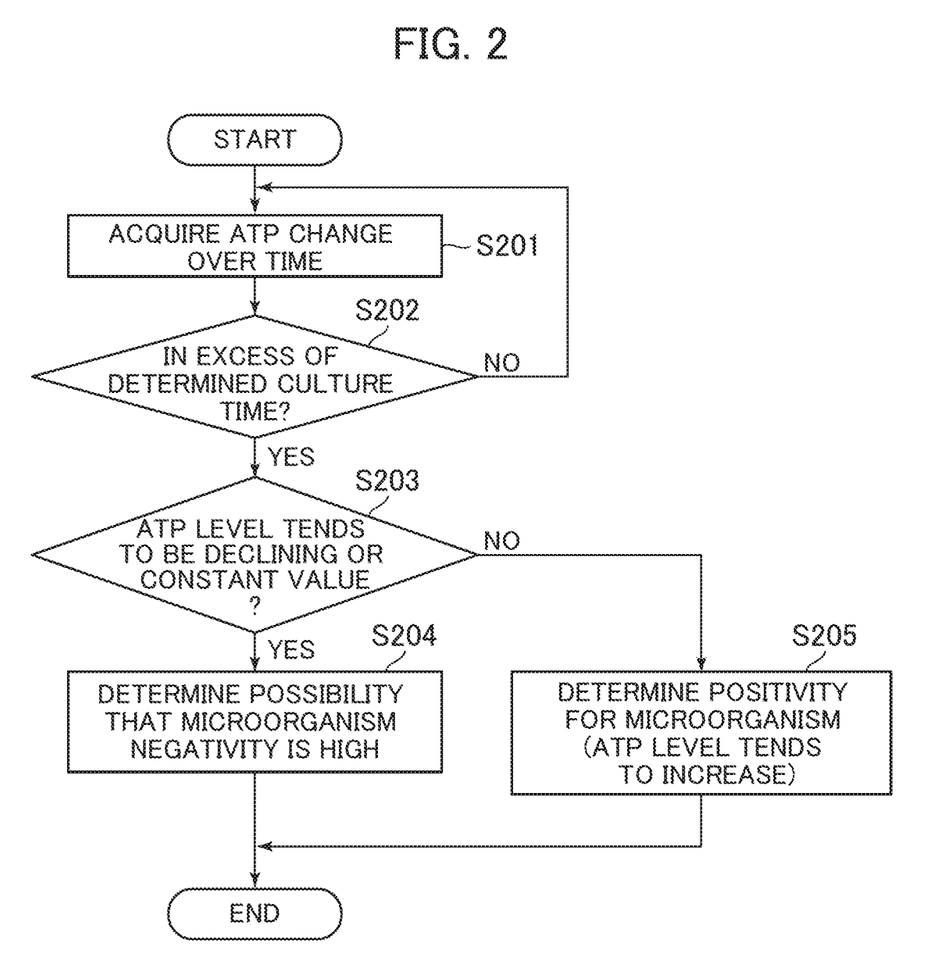
FIG. 2 illustrates a flowchart of a step for determining the presence or absence of a microorganism of the method according to the first embodiment.

FIG. 2 is a drawing describing the step for determining the presence or absence of the microorganism in the test sample in Step S105 of FIG. 1. In Step S201, as shown in FIG. 2, the change of the ATP level over time is acquired from each culture test solution.

In Step S202, it is determined whether or not the time when it becomes possible to determine the presence or absence of the microorganism has been exceeded. The time when it becomes possible to determine the presence or absence of the microorganism is the time in which the cells contained in the test sample die, and may be different depending on the cell type and the cell concentration, thus, it may be tested and determined in advance.

In Step S203, it is determined whether the change of the ATP level over time after the time when it becomes possible to determine the presence or absence of the microorganism tends to be a declining or a constant value, or tends to increase. This can be achieved by, for example, determining the slope between two different points.

In Step S204, when the ATP level in Step S203 tends to be a declining or a constant value, the likelihood that no microorganism is contained in the culture test solution is high, thus, it can be determined that the likelihood that the test sample is negative for the microorganism is high. In Step S205, when the ATP level in Step S203 tends to increase, a microorganism may be contained in the culture test solution, thus, it is determined that the test sample is positive for the microorganism.

The method for culturing a test sample in a microorganism culture medium, and detecting a microorganism in a test sample based on the acquired change of the ATP level over time according to the present disclosure has the effect which acquires the ATP level derived from the microorganism even if cells are present in the test sample. Furthermore, it is possible to clarify the presence of a living microorganism by culturing, and it is possible to detect the microorganism even if the originally contained ATP level is low.

[Second Embodiment] Method for Determining Microorganism Negativity

Figure 4:
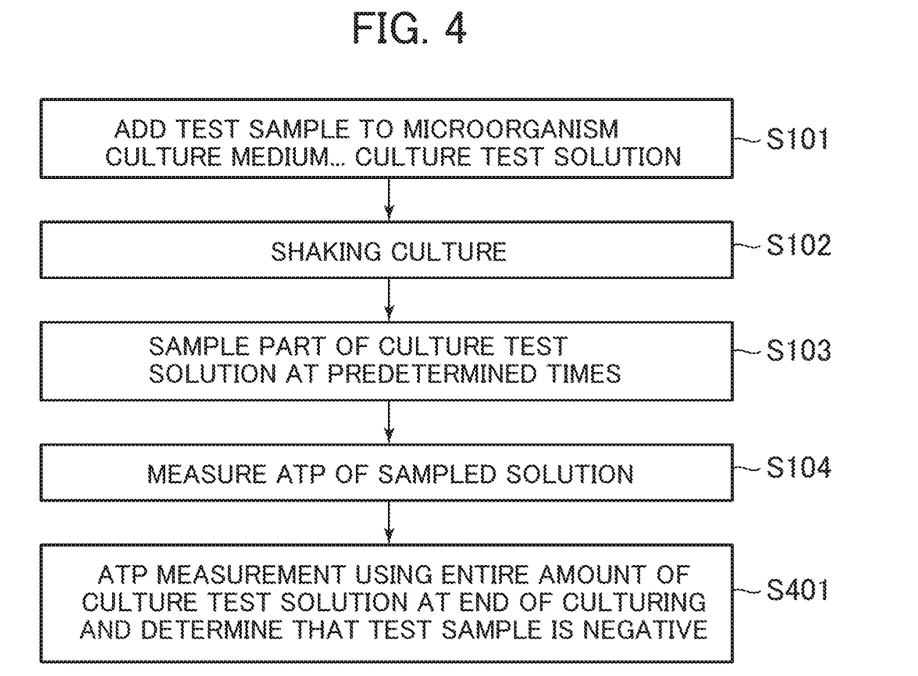
FIG. 4 illustrates a flowchart of a method according to a second embodiment.

FIG. 4 is a drawing describing the method for determining microorganism negativity according to the present disclosure.

Steps S101 to S104 are the same as Steps S101 to S104 of FIG. 1. In Step S401, the ATP level of the entire amount of the culture test solution remaining from the sampling at the end of culturing is measured. A known method such as performing the ATP luminescence measurement method after concentrating using, for example, a membrane filter may be used as the ATP measurement method for the entire amount of the culture test solution.

Figure 5:
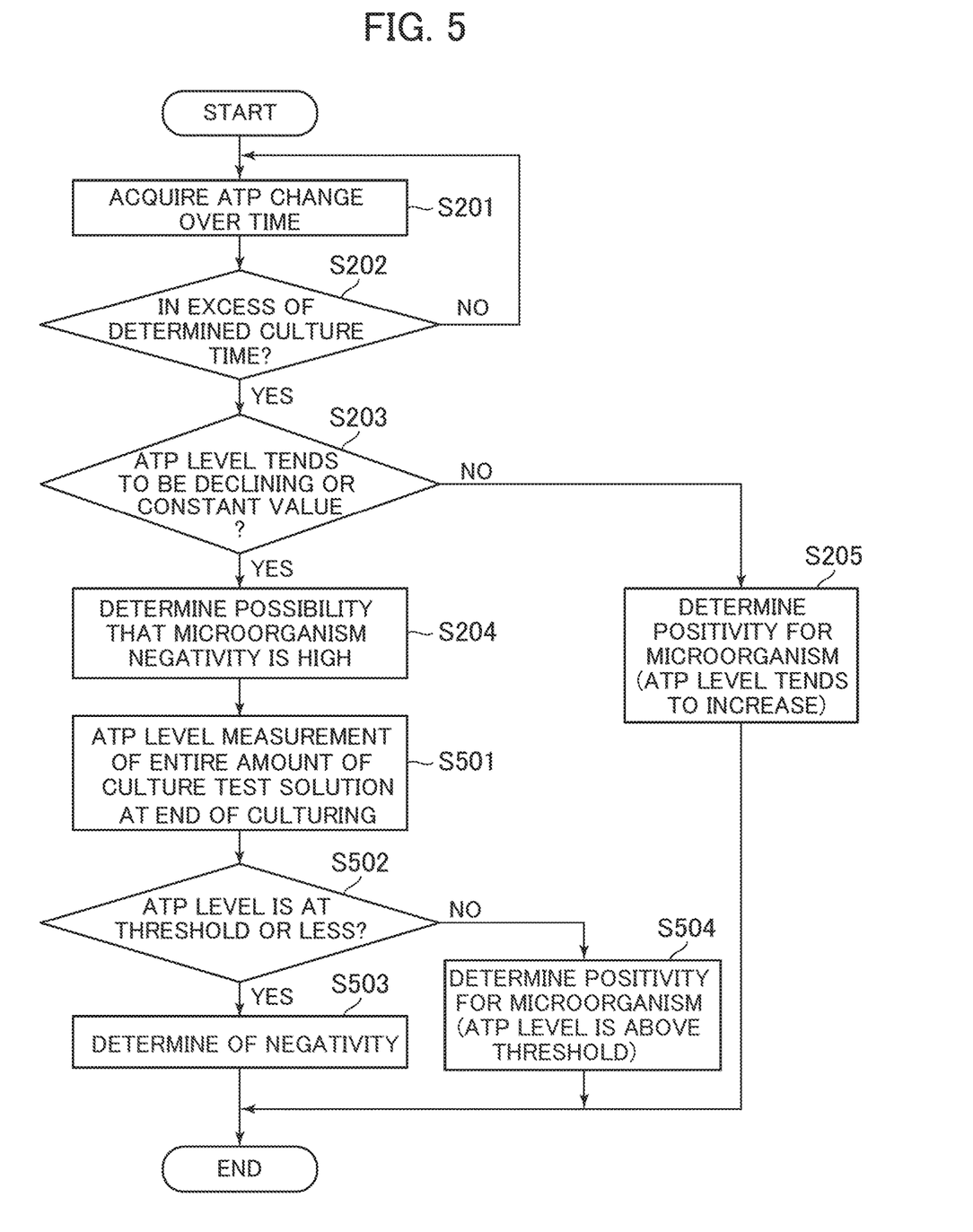
FIG. 5 illustrates a flowchart of a step for determining the presence or absence of a microorganism of the method according to the second embodiment.

FIG. 5 is a drawing describing the step of determining that the test samples in Step S401 of FIG. 4 are negative for the microorganism. Steps S201 to S205 are the same as Steps S201 to S205 of FIG. 2. In Step S204, the test sample for which it is determined that the likelihood of being negative is high is measured for the ATP level of the entire amount of the culture test solution remaining from the sampling at the end of culturing in Step S501. When the ATP level obtained in Step S502 is equal to or less than the threshold, it means that the microorganism is not present, thus, it is determined that the test sample is negative for the microorganism in Step S503. When the ATP level obtained in Step S502 is above the threshold, it means that the microorganism is present in the test sample, thus, the test sample is determined to be positive for the microorganism in Step S504.

Microorganisms for which positivity is not determined in Step S205, and are determined to be positive in Step S504 may include, for example, slow growing microorganisms (such as *Proprionobacter acnes*), and fungi for which it is difficult to confirm the proliferation in a liquid culture medium and the like (such as *Aspergillus brasiliensis*). The threshold of Step S502 may depend on the cells contained in the test sample, and may be different depending on a plurality of factors such as the culture time (culture end time), the cell type and the cell concentration, thus, the threshold may be tested and determined in advance.

The method for culturing the test sample in the microorganism culture medium, and determining the presence or absence of the microorganism based on the ATP level of the entire amount of the culture test solution at the end of culturing of the present disclosure has the effect which can realize a determination for microorganism negativity indicating that the microorganism is not present in the test sample.

EXAMPLES

Specific examples of the embodiments of the present disclosure are described below with reference to the drawings. However, these examples are merely an example for carrying out the present disclosure, and do not limit the present disclosure.

[Example 1] Acquisition of Microorganism-Derived ATP Level

As a test sample, a cell culture solution ($10^7$/mL) containing a human T cell leukemia cell line Jurkat, which was assumed for the cell preparation, was used. SCD was used as a microorganism culture medium. The Jurkat cell solution was spiked with *Bacillus subtilis* (no more than 100 bacteria/test tube) as the microorganism positive sample, and the negative sample contained only the Jurkat cell solution.

100 μL of each test sample was added to 3 mL of SCD culture medium, and was cultured by shaking at 32.5° C. Sampling was carried out at 0 hour, 18 hours, 24 hours, 42 hours, 48 hours, and 72 hours, and 20 μL of each culture test solution was sampled. The ATP level was measured by a Rapid Microbial Testing System "Lumione BL-1000".

FIG. 3 illustrates an example of the ATP change over time. The ATP level is shown as an average value of the ATP levels (N=3) of each culture test solution, and the error bars show the standard error.

From FIG. 3, it is understood that the positive sample and the negative sample at the start of culturing both show high ATP levels. This indicates the ATP level derived from cells contained in the culture test solution. However, the ATP levels of the samples also decrease when cultured. This indicates that the cells could not grow in the microorganism culture medium and had died. In the case of this example, the determination of the presence or absence of the microorganism becomes possible 18 hours after the start of culturing when the ATP level derived from human T cells becomes sufficiently low, and if the ATP change over time after an 18-hour culture time is confirmed, the ATP level tends to decrease or become a constant value for the negative sample which does not contain the microorganism, whereas the ATP level tends to increase for the positive sample containing the microorganism. This result shows that the living microorganism contained in the positive sample proliferates, and the ATP level derived from the microorganism increased. Furthermore, the result also indicates that an originally low ATP level derived from a microorganism can be detected by culturing in the microorganism culture medium. Therefore, it is clear that it is possible to measure the ATP level derived from the microorganism even in a sample containing cells, and it is possible to determine the presence or absence of living microorganism in the sample.

[Example 2] Determination of Microorganism Negativity

As a test sample, a cell culture solution ($10^6$/mL) containing a human T cell leukemia cell line Jurkat, which was assumed for the cell preparation, was used. 3 mL of a microorganism culture medium SCD was added to 100 μL of the Jurkat cell culture solution, and cultured by shaking at 32.5° C. After 24 hours, the entire amount of the culture test solution was treated with a membrane filter, and the ATP level was acquired. Assuming a positive sample, the sample spiked with *Bacillus subtilis* (no more than 100 bacteria/test tube) after culturing for 24 hours was prepared, and the ATP level was acquired in the same manner.

Figure 6:
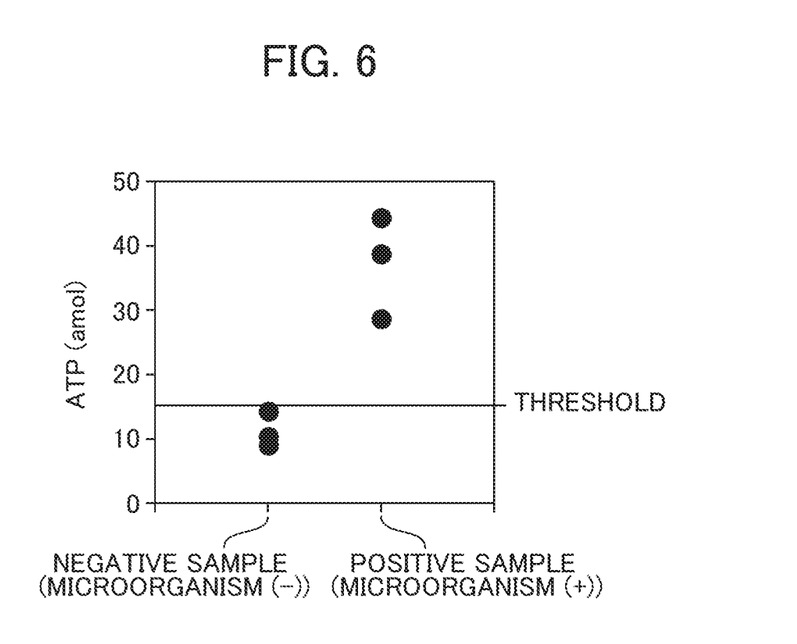
FIG. 6 is graph showing an example of a negative determination for the microorganism.

FIG. 6 shows an example of the result in which the ATP level of the entire amount of the culture test solution was measured at the end of culturing. As shown in FIG. 6, the ATP levels can be clearly distinguished between the negative sample and the positive sample. In the case of this example, it was shown that the negativity can be determined if the threshold was set at the ATP level of 15 amol. Therefore, it was clearly determined that the test sample is negative by measuring the ATP level of the entire amount of the culture test solution.

The invention claimed is:

1. A method for detecting a microorganism in a test sample comprising cells other than the microorganism targeted for detection, comprising:

a step of adding the test sample to a microorganism culture medium;

a step of culturing the microorganism culture medium comprising the test sample such that the cells in the test sample die after a period of time being cultured in the microorganism culture medium and, when the test sample is contaminated with the microorganism, such that the microorganism proliferates in the test sample after a certain period of time being cultured in the microorganism culture medium;

a step of sampling a part of the culture medium at a set of predetermined times;

a step of acquiring an adenosine triphosphate (ATP) level of the sampled culture medium at each of the set of predetermined times;

a step of detecting that the test sample is likely to be negative for the microorganism based on a change of the ATP level over the set of predetermined times being a declining or a constant value;

a step of concentrating the culture medium using a membrane filter;

after the step of concentrating the culture medium using a membrane filter, a step of acquiring the ATP level of the entire amount of the concentrated culture medium after culturing; and a step of determining a presence or absence of the microorganism in the test sample based on the ATP level of the entire amount of the culture medium after culturing, the step of determining the presence or absence of the microorganism in the test sample based on the ATP level of the entire amount of the culture medium after culturing comprises, when the ATP level of the entire amount of the culture medium after culturing is below a threshold value, determining the test sample to be negative for the microorganism, and, when the ATP level of the entire amount of the culture medium after culturing is above a threshold value, determining the test sample to be positive for the microorganism.

2. The method according to claim 1, wherein the microorganism is at least one microorganism selected from the group consisting of bacteria and fungi.

3. The method according to claim 1, wherein the test sample is at least one selected from the group consisting of blood, urine, bone marrow fluid, semen, milk, amniotic fluid, tears, biopsy tissue, cell culture solution, and cell culture supernatant.

4. The method according to claim 1, wherein the test sample is a sample derived from at least one living organism selected from the group consisting of animals, plants, and insects.

5. The method according to claim 1, wherein the acquisition of the ATP level is performed by an ATP luminescence measurement method.

* * * * *